(12) United States Patent
Charles et al.

(10) Patent No.: US 10,441,929 B2
(45) Date of Patent: Oct. 15, 2019

(54) AUTOMATED PAINT MIXING AND VERIFICATION SYSTEM AND METHODS

(71) Applicant: Walmart Apollo, LLC, Bentonville, AR (US)

(72) Inventors: Kevin Matthew Charles, Bentonville, AR (US); Michael Lawerance Payne, Centerton, AR (US); Jimmie Russell Clark, Fayetteville, AR (US)

(73) Assignee: Walmart Apollo, LLC, Bentonville, AR (US)

( * ) Notice: Subject to any disclaimer, the term of this patent is extended or adjusted under 35 U.S.C. 154(b) by 160 days.

(21) Appl. No.: 15/794,692

(22) Filed: Oct. 26, 2017

(65) Prior Publication Data

US 2018/0117550 A1   May 3, 2018

Related U.S. Application Data

(60) Provisional application No. 62/415,846, filed on Nov. 1, 2016.

(51) Int. Cl.
| | | |
|---|---|---|
| *B01F 13/10* | (2006.01) | |
| *G01N 21/3577* | (2014.01) | |
| *G01N 21/359* | (2014.01) | |
| *B01F 15/00* | (2006.01) | |
| *B01F 15/02* | (2006.01) | |
| *G01N 21/25* | (2006.01) | |
| *G01J 3/02* | (2006.01) | |
| *G01J 3/10* | (2006.01) | |
| *G01J 3/46* | (2006.01) | |

(Continued)

(52) U.S. Cl.
CPC ..... *B01F 13/1063* (2013.01); *B01F 15/00214* (2013.01); *B01F 15/00272* (2013.01); *B01F 15/0254* (2013.01); *G01J 3/0264* (2013.01); *G01J 3/0291* (2013.01); *G01J 3/108* (2013.01); *G01J 3/463* (2013.01); *G01J 3/50* (2013.01); *G01N 21/255* (2013.01); *G01N 21/359* (2013.01); *G01N 21/3577* (2013.01); *B01F 2215/005* (2013.01); *B65D 83/42* (2013.01); *G01N 2201/06113* (2013.01)

(58) Field of Classification Search
CPC ............ B01F 13/1063; B01F 15/00214; B01F 15/00272; B01F 15/0254; B01F 2215/005; B65D 83/42; G01J 3/0264; G01J 3/0291; G01J 3/108; G01J 3/463; G01J 3/50; G01N 21/255; G01N 21/3577; G01N 21/359; G01N 2201/06113
See application file for complete search history.

(56) References Cited

U.S. PATENT DOCUMENTS 3,020,795 A * 2/1962 McKinney ............. G01N 21/53
356/246
3,601,589 A * 8/1971 McCarty ................... G01J 3/46
356/402

(Continued)

*Primary Examiner* — Tony G Soohoo
(74) *Attorney, Agent, or Firm* — McCarter & English, LLP; David R. Burns

(57) ABSTRACT

An automated system for automatically mixing and verifying paint is described. The system may include a kiosk configured to automatically add a paint of a second color to a paint container holding a first color of paint so as to produce a requested third color of paint. The system may further verify that the mixed paint color is the requested paint color using a laser to perform verification.

20 Claims, 6 Drawing Sheets

(51) Int. Cl.
*G01J 3/50* (2006.01)
*B65D 83/42* (2006.01)

(56) References Cited

U.S. PATENT DOCUMENTS

| | | | | |
|---|---|---|---|---|
| 4,335,759 A | * | 6/1982 | Pattiniemi | B01F 13/1058 141/329 |
| 4,403,866 A | * | 9/1983 | Falcoff | B01F 13/1055 366/132 |
| 4,494,677 A | * | 1/1985 | Falcoff | B01F 15/0454 222/63 |
| 5,203,387 A | | 4/1993 | Howlett et al. | |
| 6,000,837 A | * | 12/1999 | Randsborg | B01F 13/1055 366/141 |
| 6,744,513 B2 | * | 6/2004 | Kubo | G01J 3/0251 356/402 |
| 7,612,129 B2 | | 11/2009 | Friel et al. | |
| 7,815,361 B2 | * | 10/2010 | Lindblom | B01F 11/0022 366/136 |
| 8,666,540 B2 | | 3/2014 | Milhorn | |
| 9,205,941 B2 | | 12/2015 | Bush et al. | |
| 2001/0047309 A1 | * | 11/2001 | Bartholomew | B01F 13/1063 700/233 |
| 2003/0019885 A1 | * | 1/2003 | Luehrsen | B01F 13/1055 222/94 |
| 2009/0099695 A1 | | 4/2009 | Trevino, III et al. | |
| 2009/0112371 A1 | * | 4/2009 | Hughes | G05D 11/132 700/282 |
| 2009/0228367 A1 | | 9/2009 | Hughes et al. | |
| 2014/0174595 A1 | * | 6/2014 | Milhorn | B01F 13/1055 141/9 |
| 2015/0178815 A1 | | 6/2015 | Cassidy | |
| 2018/0117550 A1 | * | 5/2018 | Charles | G01N 21/255 |

\* cited by examiner

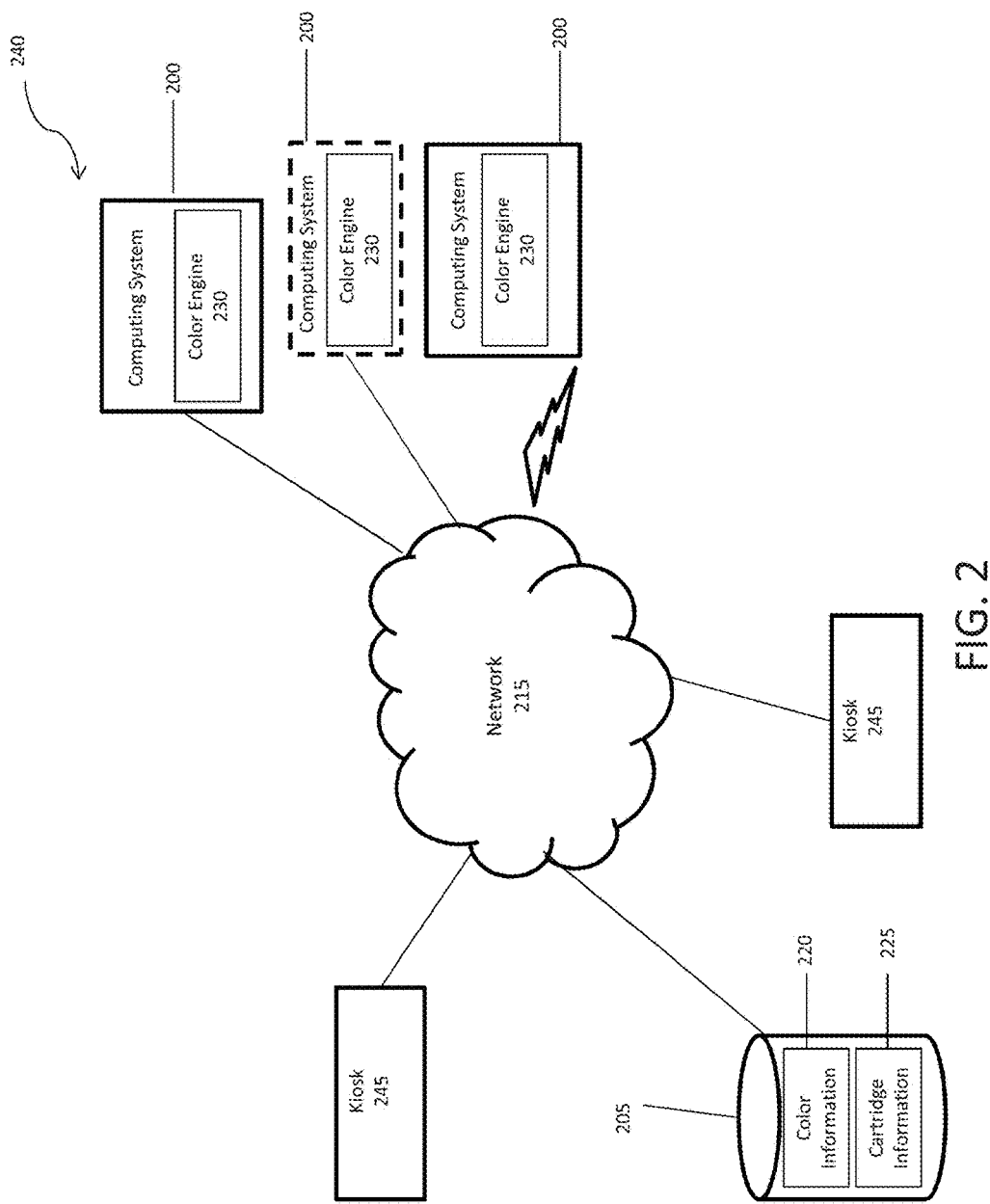

AUTOMATED PAINT MIXING AND VERIFICATION SYSTEM AND METHODS

CROSS-REFERENCE TO RELATED PATENT APPLICATIONS

This application claims priority to U.S. Provisional Application No. 62/415,846 filed on Nov. 1, 2016, the content of which is hereby incorporated by reference in its entirety.

BACKGROUND

Facilities may include paint mixing machines and systems. To produce a paint of a desired color, paints of different colors may be mixed together and the result inspected to determine if the mixed color matches the requested color.

SUMMARY

In one embodiment, a paint color mixing system includes a processing device equipped with a processor and a paint container including an aperture. The paint container contains a paint of a first color. The system further includes a self-service kiosk in communication with the processing device and including an interactive display, a nozzle and a laser. The kiosk is configured to support the paint container by inserting the nozzle into the aperture of the paint container and to inject a paint of a second color into the paint container through the nozzle so as to attempt to produce a paint of a third color. The third color is requested by a user via the interactive display. The kiosk is further configured to mix the paint of the second color with the paint of the first color in the paint container and to project a transmission from the laser through the aperture into the paint container to determine a color of the mixed paint inside the paint container. The paint container remains in a sealed condition during the transmission. The processing device is configured to verify programmatically whether the determined color of the mixed paint in the paint container is the same as the requested third color of paint and to transmit a result of the verifying to the interactive display.

In another embodiment, a paint color mixing method is performed in a self-service paint mixing kiosk equipped with an interactive display, a nozzle and a laser. The method includes providing a paint container that includes an aperture and contains a paint of a first color. The method further includes inserting the nozzle into the aperture of the paint container. The nozzle provides support for the paint container in the kiosk. The method also includes injecting a paint of a second color into the paint container through the nozzle so as to attempt to produce a paint of a third color. The third color is requested by a user via the interactive display. The method further includes, mixing the paint of the second color with the paint of the first color in the paint container and projecting a transmission from the laser through the aperture into the paint container to determine a color of the mixed paint inside the paint container. The paint container remains in a sealed condition during the transmission of the laser. The method further includes verifying, via a processing device in communication with the kiosk whether the determined color of the mixed paint in the paint container is the same as the paint of the third color and transmitting a result of the verifying to the interactive display.

In one embodiment, a paint color verification system includes a processing device equipped with a processor and a paint container including an aperture. The paint container contains a paint. The system further includes a structural device in communication with the processing device that includes an interactive display, a nozzle and a laser. The structural device is configured to support the paint container by inserting the nozzle into the aperture of the paint container and to project a transmission from the laser through the aperture into the paint container to determine a color of the paint inside the paint container. The paint container remains in a sealed condition during the transmission. The processing device is configured to receive a request to determine whether the color of the paint in the paint container is a first color, to verify programmatically whether the determined color of the paint in the paint container is the same as the second color and to transmit results of the verification.

BRIEF DESCRIPTION OF THE FIGURES

Illustrative embodiments are shown by way of example in the accompanying figures and should not be considered as a limitation of the present disclosure. The accompanying figures, which are incorporated in and constitute a part of this specification, illustrate one or more embodiments of the invention and, together with the description, help to explain the invention. In the figures:

FIG. 2 is a block diagrams illustrating an automated paint mixing system according to an exemplary embodiment;

DETAILED DESCRIPTION

Described in detail herein is an automated paint mixing system. In one embodiment a paint container can be placed in a kiosk. The paint container can contain paint of a first color and can include an aperture on the top or on the side of the container. In one embodiment, the aperture may be centrally located in a lid on top of the paint container. The paint container can be secured by a nozzle of the kiosk inserted into the aperture and the kiosk can receive instructions to convert the first color of the paint in the paint container to a requested color. The kiosk can store paint cartridges including paints of various pigments. Upon receiving a processed request as described further herein, paint from the paint cartridges can be injected by the kiosk through the nozzle into the paint container. A second color of paint from the paint cartridges can be automatically mixed by the kiosk to generate the requested color. Following mixing, a laser disposed within the nozzle can project a transmission through the aperture into the paint container, while the paint container remains in a sealed condition. The laser apparatus can determine the mixed color and a processing device in communication with the kiosk can verify whether the mixed color is the same as the requested second color.

Figure 1A:
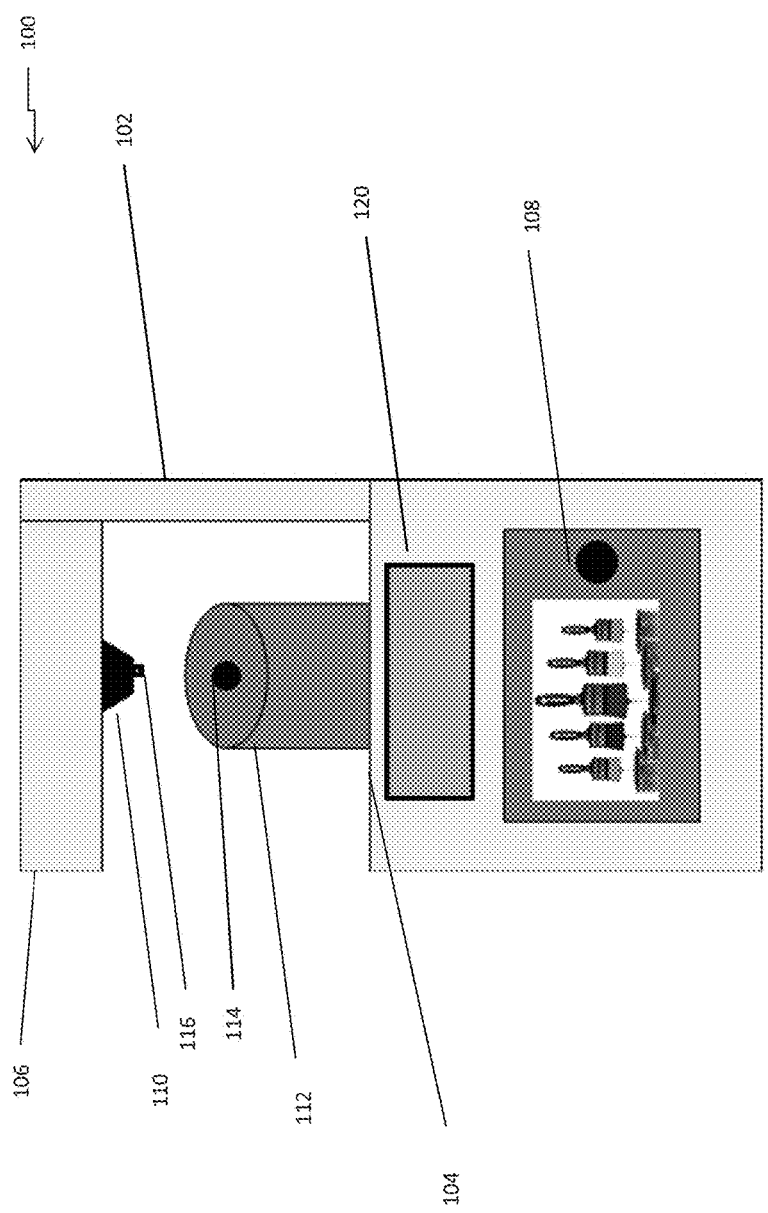
FIG. 1A is a block diagram of a self-service paint mixing kiosk in accordance with an exemplary embodiment.
Figure 1B:
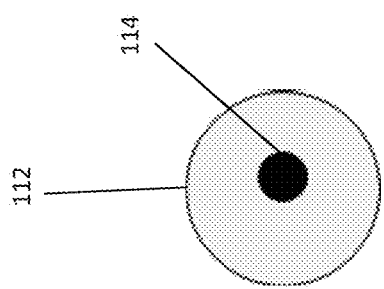
FIG. 1B is a block diagram of an exemplary paint container in accordance with in accordance with an exemplary embodiment.

FIG. 1A is a block diagram of an automated self-service paint mixing kiosk in accordance with an exemplary embodiment. In the exemplary embodiment, a self-service paint mixing kiosk 100 can be disposed in a facility. The self-service kiosk 100 can include a side wall 102, a base 104, a top wall 106, a storage area 108, and a nozzle 110 extending from the top wall 106. The nozzle may include an integrated laser 116. Alternatively, the laser 116 may be separate from the nozzle 110. The base 104 can support a paint container 112. The side wall 102 can extend perpendicularly from the base 104 and the top wall 106 can extend laterally from the side wall 102 and can be disposed parallel to the base 104. The base 104, top wall 106 and side wall 102 can form a housing to hold and support the paint container 112 during the mixing operations described herein. The paint container 112 can include a paint of a first color. For example, the paint container may contain a known base color of paint. The paint container can include an aperture 114 centrally located on the top of the paint container 112. The storage area 108 can store various paint cartridges of various pigments of paint. FIG. 1B is a top view of the paint container 112 in accordance with in accordance with an exemplary embodiment. With reference to FIG. 1B, the paint container 112 can include a aperture 114 centrally located in the lid of the paint container 112. The aperture 112 can provide access to the paint inside the paint container 112. The lid can remain completely sealed and secured to the paint container 112 during the mixing and verifying operations described herein. In some embodiments, the aperture 114 can also be on the side of the paint container.

Turning back to FIG. 1A, the self-service kiosk 100 can receive a request to change the paint inside the paint container from a first color to a requested color. In some embodiments, the self-service kiosk 100 can also receive a request through a user interface 120 provided by the kiosk. For example, the self-service kiosk 100 may include a touch screen user interface at which a user may select a requested color. The self-service kiosk 100 may also receive a request for paint additives such as mold resistance, fingerprint resistance, high traffic or magnetic flakes to be included in the paint container. The self-service kiosk 100 can programmatically determine a second color to mix with the first color already in the paint container to generate the requested (third) color. The self-service kiosk 100 can select a paint cartridge of the determined second color from the storage are 108. In some embodiments, more than one paint cartridge can be selected. The paint of the second color can travel from the storage area 108, through the side wall 102 and the top wall 106 and through the nozzle 110. The nozzle 110 can be configured to be secured to and/or inserted into the aperture 114 of the paint container 114. The paint of a second color can be injected through the nozzle and the aperture 114 into the paint container 112. For example, in one embodiment, a paint dispensing tube may be automatically extended by the kiosk through the nozzle to inject paint into the container and then withdrawn following its dispensing of paint. In another embodiment, the paint dispensing tube may be affixed to the nozzle. The paint of the second color can be mixed in with the first color to attempt to generate a requested (third) color. The self-service kiosk 100 may include mechanical mixing means as is known in the art to allow the kiosk to shake the paint container 112 for a predetermined amount of time to mix the first color and the second color. During the mixing process, the attachment of the nozzle to the paint container may provide additional support to the paint container.

Subsequent to mixing the first and second color, the self-service kiosk 100 can verify the mixed color in the paint container matches the requested (third) color. The self-service kiosk 100 can project a transmission from a laser 116 disposed within the nozzle 110 through the aperture into the paint container 112 to verify the mixed color matches the requested color. The nozzle 110 can be tightly secured to the aperture 114 so that light does not enter through the aperture 114 into the paint container 112. The laser 116 can therefore verify the color of the mixed paint without lifting the lid of the paint container 112. In one embodiment, the laser 116 can use Near-Infrared Spectroscopy (NIRS) to verify the mixed color matches the requested second color. NIRS is interaction between a sample (e.g. the mixed paint color) and infrared light that has been dispersed (e.g. the transmission) into individual wavelengths, usually by a prism. In response to verifying that the mixed color matches the requested color the self-service kiosk 100 can automatically and mechanically remove the paint container from the housing. In response to determining that the mixed paint does not match the requested color, the self-service kiosk 100 can inject a paint of a fourth color into the paint container to attempt to generate the requested color. In some embodiments, the paint container 112 can be a spray paint can or other type of container containing paint. In some embodiments, paint can be mixed into the paint in the spray paint can prior to the pressurization. Alternatively, paint can be mixed into the paint in the spray paint can subsequent to pressurization.

In some embodiments, the laser 116 can verify the color of a paint within a paint container 112 which is supported by structures other than the self-service kiosk 100, such as a spray paint gun or air powered paint guns which can store a plurality of paint containers.

Figure 1C:
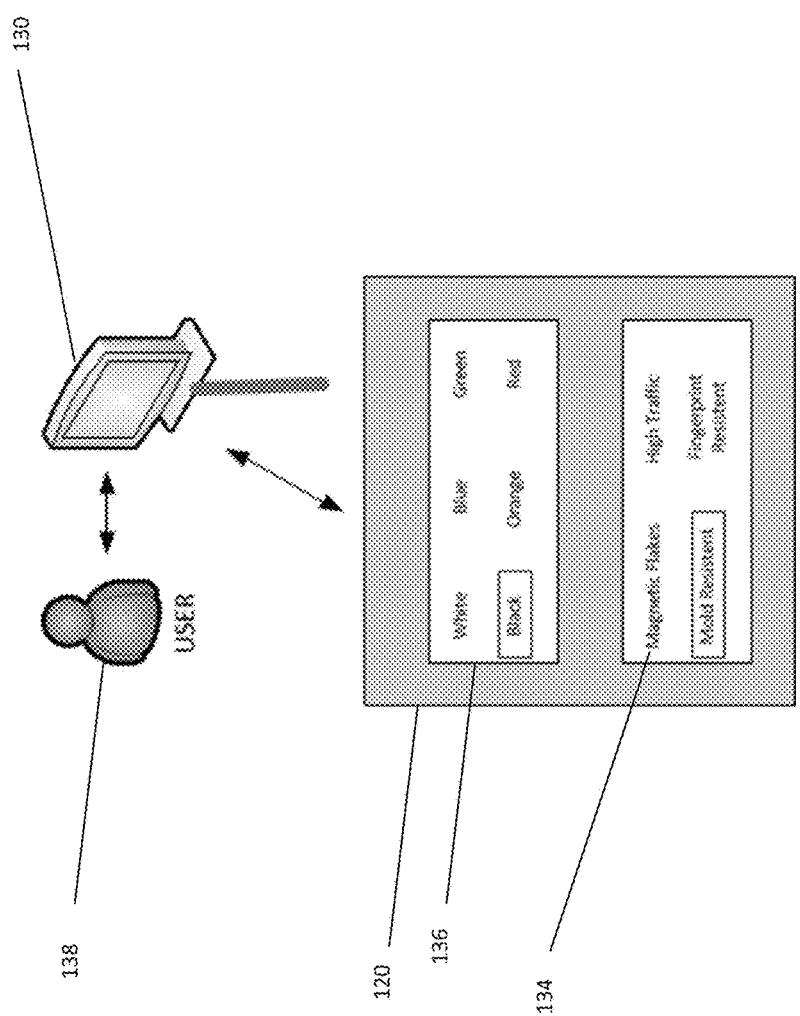
FIG. 1C is a block diagram of a user interface at the kiosk in accordance with an exemplary embodiment.

FIG. 1C is a block diagram of a user interface 120 at the kiosk in accordance with an exemplary embodiment. The self-service kiosk as shown in FIG. 1A can include a display 130 with a user interface 120. A user 138 can interact with the user interface 120 to select a color of paint for the paint container. For example, the user interface 138 can be an interactive interface and can include a display for color options 136. As a non-limiting example, the user can select colors such as White, Black, Green, Black, Orange and Red. The user 138 can also be presented options for paint additives 134. As a non-limiting example, the options for paint additives can be magnetic flakes, high traffic, mold resistant and finger print-resistant. For example, the user 138 can make selections to change the color within the paint container to black and to include magnetic flakes in the paint. The computing system can receive the selections. In some embodiment, subsequent to mixing and verifying the color in the paint container the user interface may display the verified color within the paint container.

In one embodiment, a scanner (not shown) can be disposed at the self-service kiosk and the user can scan a color using the scanner and the self-service kiosk can determine the scanned color and then attempt to change the color of the paint inside the paint container to the scanned color by mixing in an appropriate color of paint. In another embodiment, instead of a scanner disposed at the kiosk, a user may take a picture of a paint color and transmit the image to the kiosk to allow the kiosk to programmatically determine the particular color selection.

FIG. 2 illustrates an exemplary automated paint mixing system in accordance with an exemplary embodiment. The automated paint mixing system 240 can include one or more databases 205, one or more computing systems 200 and multiple instances of the kiosks 245. The kiosks 245 can be self-service paint mixing kiosks. In exemplary embodiments, the computing system 200 can be in communication with the databases 205 and multiple instances of the kiosks 245 via a communications network 215. The computing system 200 can implement at least one instance of the color engine 230.

In an example embodiment, one or more portions of the communications network 215 can be an ad hoc network, an intranet, an extranet, a virtual private network (VPN), a local area network (LAN), a wireless LAN (WLAN), a wide area network (WAN), a wireless wide area network (WWAN), a metropolitan area network (MAN), a portion of the Internet, a portion of the Public Switched Telephone Network (PSTN), a cellular telephone network, a wireless network, a WiFi network, a WiMax network, another type of network, or a combination of two or more such networks.

The computing system 200 includes one or more computers or processors configured to communicate with the databases 205 and kiosks 245 via the network 215. The computing system 200 hosts one or more applications configured to interact with one or more components of the automated paint mixing system 240. The databases 205 may store information/data, as described herein. For example, the databases 205 can include color information database 220 and cartridge information database 225. The color information database 220 can store information associated with color pigments. The cartridge information database 225 can include information associated with paint cartridges stored in the kiosks 245. The databases 205, kiosks 245 and computing system 200 can be located at one or more geographically distributed locations from each other. Alternatively, the databases 205 can be included within computing system 200.

In exemplary embodiments, the computing system 200 can receive from an instance of the kiosk 245, data regarding a first color of paint contained inside a paint container and a user selection of a requested color and/or a paint additive. The computing system 200 can receive information regarding the user's desire to change the first color of the paint in the paint container to the second color and/or add the paint additive into the paint in the paint container. In response to receiving the information, the computing system 200 can execute the paint engine 230. The paint engine 230 can determine which color(s) need to be mixed into the existing paint in the paint container in order to attempt to generate the requested color. Additionally, the paint engine 230 can determine which paint additives to add to the paint. For example, the paint engine 230 can query the color information database 220 using data regarding the first color and the requested color selection from the user to determine which pigments need to be mixed into the first color to generate the requested color. Once the determination is made, the paint engine 230 can query the cartridge information database 225 using a location of the kiosk 245 to determine which cartridges stored at the kiosk 245 correspond with the determined pigments. The paint engine 230 can instruct the kiosk 245 to inject and mix the paint from the paint cartridges corresponding with the determined pigments and/or add the paint additives into the paint container holding paint of the first color. Subsequent to mixing the paint from the paint cartridges the color engine 230 can instruct the kiosk 245 to project a transmission, via the laser, into the paint container to verify the mixed color matches the requested (third)color. Alternatively, the kiosk may be programmed in advance to automatically perform the verification without receiving further instructions. The kiosk 245 can transmit a signal to the computing system 200 in response to projecting the transmission into the paint container. The signal can indicate a determined color of the mixed paint in the paint container. The color engine 230 can determine whether the determined color matches the requested (third)color based off of the received signal. In response to determining that the mixed color in the paint container matches the requested color, the color engine 230 can display the mixed color on the display of the kiosk 245 and instruct the kiosk to automatically remove the paint container from the housing in the kiosk 245. Alternatively, in response to determining the mixed color does not match the requested color, the color engine 230 can query the color information database 220 to determine which pigments need to be added to the paint to generate the requested color. The color engine 230 can instruct the kiosk 245 to inject and mix the paint from the paint cartridges corresponding to the newly determined pigments. In some embodiments, the color engine 230 can also verify any paint additives added into the paint based on the received signal from the kiosk 245.

As a non-limiting example, the kiosk 245 can be a self-service kiosk disposed in a retail store. A customer can place a paint container, containing a paint of a first color at the kiosk 245 and input the first color of the paint. The customer may also select a requested color at the kiosk 245 to which the customer wishes to alter the paint in the paint container. The customer can also select paint additives to be added into the paint. Alternatively, the container with paint of the first color may be selected by the kiosk based on and following the user selection. For example, if the user selected orange paint and the computing system knew the kiosk had available yellow paint, the kiosk may be instructed to select a container with a base of red paint into which the yellow paint could be inserted in order to produce the requested orange paint (red+yellow=orange). The kiosk 245 can transmit the input information of the first color and/or paint additives to the computing system 200. The computing system 200 can receive the user selection and associated information. The computing system 200 can execute the color engine 245, in response to receiving the instructions. The color engine 245 can query the color information database 220 to retrieve the different pigments needed to change the first color to the requested color and/or the additives needed to add into the paint. The color engine 230 can query the cartridge information database 225 to determine the which paint cartridges stored at the kiosk 245 correspond to the determined pigments (if the pigments needed are unavailable, in one embodiment a message to that effect may be displayed on the user interface 120). The color engine 230 can instruct the kiosk 245 to inject and mix the paint from the determined paint cartridges in the paint container. Subsequent to mixing the paint, the color engine 230 can instruct the kiosk 245 to project a transmission via the kiosk's laser, into the paint container to attempt to verify the mixed color matches the requested color. Upon verification of the correct color, the color engine 230 may prompt the display of the kiosk to display the new color of the paint and automatically remove paint container from the housing of the kiosk. In one embodiment, the customer can complete a purchase transaction for the new paint at the kiosk 245.

Figure 3:
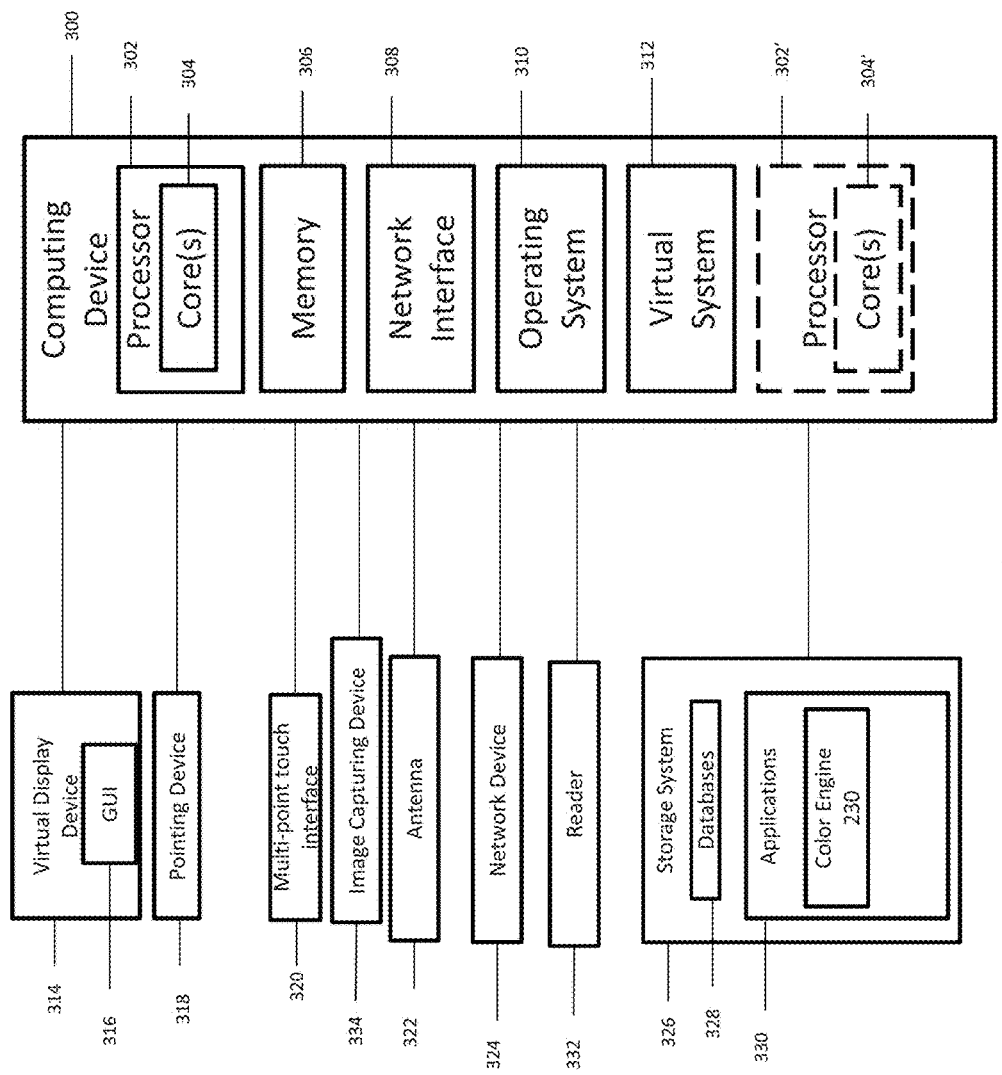
FIG. 3 is a block diagram illustrating an exemplary computing device in accordance with an exemplary embodiment.

FIG. 3 is a block diagram of an example computing system for implementing exemplary embodiments of the present invention. Computing system 240 may include one or more of computing device(s) 300. Computing device 300 can execute color engine 230. The computing device 300 includes one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more flash drives, one or more solid state disks), and the like. For example, memory 306 included in the computing device 300 may store computer-readable and computer-executable instructions or software (e.g., applications 330 such as the color engine 230) for implementing exemplary operations of the computing device 300. The computing device 300 also includes configurable and/or programmable processor 302 and associated core(s) 304, and optionally, one or more additional configurable and/or programmable processor(s) 302' and associated core(s) 304' (for example, in the case of computer systems having multiple processors/cores), for executing computer-readable and computer-executable instructions or software stored in the memory 306 and other programs for implementing exemplary embodiments of the present disclosure. Processor 302 and processor(s) 302' may each be a single core processor or multiple core (304 and 304') processor. Either or both of processor 302 and processor(s) 302' may be configured to execute one or more of the instructions described in connection with computing device 300.

Virtualization may be employed in the computing device 300 so that infrastructure and resources in the computing device 300 may be shared dynamically. A virtual machine 312 may be provided to handle a process running on multiple processors so that the process appears to be using only one computing resource rather than multiple computing resources. Multiple virtual machines may also be used with one processor.

Memory 306 may include a computer system memory or random access memory, such as DRAM, SRAM, EDO RAM, and the like. Memory 306 may include other types of memory as well, or combinations thereof.

A user may interact with the computing device 300 through a visual display device 314, such as a computer monitor, which may display one or more graphical user interfaces 316, multi touch interface 320 and a pointing device 318.

The computing device 300 may also include one or more storage devices 326, such as a hard-drive, CD-ROM, or other computer readable media, for storing data and computer-readable instructions and/or software that implement exemplary embodiments of the present disclosure (e.g., applications). For example, exemplary storage device 326 can include one or more databases 328 for storing information regarding color pigment and paint cartridges stored in the kiosks. The databases 328 may be updated manually or automatically at any suitable time to add, delete, and/or update one or more data items in the databases.

The computing device 300 can include a network interface 308 configured to interface via one or more network devices 324 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. In exemplary embodiments, the computing system can include one or more antennas 322 to facilitate wireless communication (e.g., via the network interface) between the computing device 300 and a network and/or between the computing device 300 and other computing devices. The network interface 308 may include a built-in network adapter, network interface card, PCMCIA network card, card bus network adapter, wireless network adapter, USB network adapter, modem or any other device suitable for interfacing the computing device 300 to any type of network capable of communication and performing the operations described herein.

The computing device 300 may run operating system 310, such as versions of the Microsoft® Windows® operating systems, different releases of the Unix and Linux operating systems, versions of the MacOS® for Macintosh computers, embedded operating systems, real-time operating systems, open source operating systems, proprietary operating systems, or other operating systems capable of running on the computing device 300 and performing the operations described herein. In exemplary embodiments, the operating system 310 may be run in native mode or emulated mode. In an exemplary embodiment, the operating system 310 may be run on one or more cloud machine instances.

Figure 4:
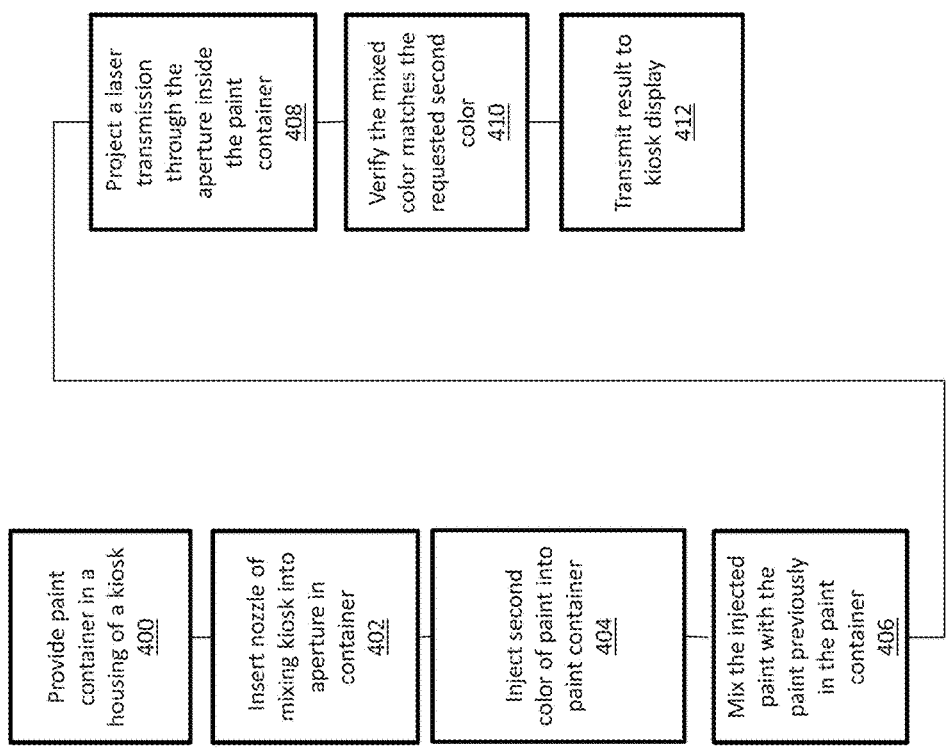
FIG. 4 is a flowchart illustrating an exemplary process in accordance with an exemplary embodiment.

FIG. 4 is a flowchart illustrating a the automated paint mixing process according to exemplary embodiment. In operation 400, a paint container (e.g. paint container 112 as shown in FIG. 1A-B) can be placed in a housing of a kiosk (e.g. kiosk 100 as shown in FIG. 1A). The paint container can include an aperture (e.g. aperture 114 as shown in FIG. 1A-B) on the top or on the side of the paint container and can contain paint of a first color. A user can interact with an interactive user interface (e.g. user interface 120 as shown in FIGS. 1A and 1C) of a display (e.g. display 130 as shown in FIG. 1C) of the kiosk to input a selection for changing the first color of the paint in the container to a requested color. The kiosk can transmit the first color (i.e. the paint already in the paint container), and a selection of a target color to the computing system (e.g. computing system 200 as shown in FIG. 2). The computing system can execute a color engine (e.g. color engine 230 as shown in FIG. 2) in response to receiving the instructions. The color engine can query the color information database (e.g. color information database 220 as shown in FIG. 2) to determine which pigments are needed to convert the first color to the requested color. In one embodiment, the color engine can query the cartridges database (e.g. cartridges database 220 as shown in FIG. 2) to determine which cartridges corresponding to the determined pigments needed to alter the first color of paint.

Once the color needed to perform the requested transformation has been determined, instructions are sent from the computing system to the kiosk to inject the container of paint with the determined color. In operation 402, a nozzle from the kiosk is inserted into the aperture of the paint container. In operation 404, the determined color of paint from a paint cartridge or other source corresponding to the determined color pigments can be injected into the paint container through the inserted nozzle (e.g. nozzle 110 as shown in FIG. 1A) disposed on the kiosk secured to the aperture. In operation 406, the kiosk can automatically mix the inserted paint with the paint of the first color that is already present in the paint container. In operation 408, a laser (e.g. laser 116 as shown in FIG. 1A) can project a transmission through the aperture inside the paint container while the paint container remains in a sealed condition. In one embodiment, the reflected signal may be used to perform NIRS. In operation 410, the kiosk can transmit a signal indicating the determined mixed color inside the paint container, based on the projection of the transmission, to the computing system which verifies whether the signal results are indicative of the requested color. For example, the color engine can query a color information database to verify whether the mixed color matches the requested second color. In operation 412, in response to determining the mixed color in the paint container matches the requested second color the color engine can prompt the user interface on the kiosk to display the result of the verification to the user.

Although the description contained herein has mentioned the use of "paint cartridges" as an additive to be mixed in the paint container, it should be understood that the embodiments of the present invention are not so limited. For example, other tints, previously mixed paints or other substances capable of being inserted into the paint container and capable of being mixed with the first color of paint to produce the requested color of paint should be considered to also be within the scope of the present invention.

In some embodiments, the kiosk can be any structural device used to verify the color of the paint inside a paint container using a laser. For example, the structural device can include a laser. The laser can project a transmission through the aperture inside the paint container while the paint container remains in a sealed condition. In one embodiment, the reflected signal may be used to perform NIRS. The structural device can transmit a signal indicating the determined color inside the paint container, based on the projection of the transmission, to the computing system which verifies whether the signal results are indicative of the requested color. The structural device and trigger an action in response to verification of the color. The computing system can transmit a verification. In another example, the structural device can be a paint gun storing multiple paint containers which can configured to release the paint in response to verification of the color of the paint inside the paint container.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a multiple system elements, device components or method steps, those elements, components or steps may be replaced with a single element, component or step. Likewise, a single element, component or step may be replaced with multiple elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the present disclosure. Further still, other aspects, functions and advantages are also within the scope of the present disclosure.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than the order shown in the illustrative flowcharts.

We claim:

1. A paint color mixing system, the system comprising:
   a processing device equipped with a processor;
   a paint container including an aperture, the paint container containing a paint of a first color;
   a self-service kiosk in communication with the processing device and including an interactive display, a nozzle and a laser, the kiosk configured to:
   support the paint container by inserting the nozzle into the aperture of the paint container;
   inject a paint of a second color into the paint container through the nozzle so as to attempt to produce a paint of a third color, the third color requested by a user via the interactive display;
   mix the paint of the second color with the paint of the first color in the paint container;
   project a transmission from the laser through the aperture into the paint container to determine a color of the mixed paint inside the paint container, the paint container remaining in a sealed condition during the transmission,
   wherein the processing device is configured to:
   verify programmatically whether the determined color of the mixed paint in the paint container is the same as the paint of the third color and,
   transmit a result of the verifying to the interactive display.

2. The system of claim 1, wherein the aperture is located in a lid on the top of the paint container.

3. The system of claim 1, wherein the aperture is on at least a first side of the paint container.

4. The system of claim 1, wherein the laser is used to perform Near-Infrared Spectroscopy (NIRS) to determine the color of the mixed paint.

5. The system of claim 1, wherein the paint container is a spray paint can.

6. The system of claim 1, wherein the kiosk is further configured to:
   receive a request for a paint additive via the interactive display.

7. The system of claim 6, wherein the kiosk is further configured to:
   select the paint of the second color based on requested paint of the third color and the requested paint additive.

8. The system of claim 1, wherein the processing device determines that at least one of more paint and a different color of paint is needed to produce the paint of the third color.

9. The system of claim 1, wherein the kiosk is further configured to:
   remove automatically the paint container from a housing in the kiosk in response to the processing device verifying that the determined color of the mixed paint in the paint container is the same as the paint of the third color requested by the user.

10. A paint color mixing method performed in a self-service paint mixing kiosk equipped with an interactive display, a nozzle and a laser, the method comprising:
    providing a paint container that includes an aperture and contains a paint of a first color;
    inserting the nozzle into the aperture of the paint container, the nozzle providing support for the paint container in the kiosk;
    injecting a paint of a second color into the paint container through the nozzle so as to attempt to produce a paint of a third color, the third color requested by a user via the interactive display;
    mixing the paint of the second color with the paint of the first color in the paint container;
    projecting a transmission from the laser through the aperture into the paint container to determine a color of the mixed paint inside the paint container, the paint container remaining in a sealed condition during the transmission;

verifying, via a processing device in communication with the kiosk whether the determined color of the mixed paint in the paint container is the same as the paint of the third color; and transmitting a result of the verifying to the interactive display.

11. The method of claim 10, wherein the aperture is located in a lid on the top of the paint container.

12. The method of claim 10, wherein the aperture is located on at least a first side of the paint container.

13. The method of claim 10, wherein laser is used to perform Near-Infrared Spectroscopy (NIRS) to determine the color of the mixed paint.

14. The method of claim 10, wherein the paint container is a spray paint can.

15. The method of claim 10, further comprising:
receiving a request on the interactive display of the kiosk for a paint additive.

16. The method of claim 15, further comprising:
selecting programmatically, at the kiosk, the paint of the second color based on the requested third color and the requested paint additive.

17. The method of claim 10, further comprising:
determining, with the processing device, that at least one of more paint and a different color of paint is needed to produce the paint of the third color.

18. The method of claim 10, further comprising:
removing automatically the paint container from a housing in the self-service kiosk in response to the processing device verifying that the determined color of the mixed paint in the paint container is the same as the paint of the third color requested by the user.

19. A paint color verification system, the system comprising:
a processing device equipped with a processor;
a paint container including an aperture, the paint container containing a paint;
a structural device in communication with the processing device and including an interactive display, a nozzle and a laser, the structural device configured to:
support the paint container by inserting the nozzle into the aperture of the paint container; and
project a transmission from the laser through the aperture into the paint container to determine a color of the paint inside the paint container, the paint container remaining in a sealed condition during the transmission,
wherein the processing device is configured to:
receive a request to determine whether the color of the paint in the paint container is a first color;
verify programmatically whether the determined color of the paint in the paint container is the same as the second color; and
transmit the verification.

20. A paint color verification system of claim 19, wherein the laser is used to perform Near-Infrared Spectroscopy (NIRS) to determine the color of the paint in the paint container.

* * * * *